United States Patent [19]

Halcour et al.

[11] Patent Number: 4,490,487

[45] Date of Patent: Dec. 25, 1984

[54] SO₃/IMIDE ADDUCTS, PROCESS FOR THEIR PREPARATION AND THEIR USE AS SULPHONATING AGENTS

[75] Inventors: Kurt Halcour; Peter-Michael Lange; Rudolf Wagner, all of Leverkusen, Fed. Rep. of Germany

[73] Assignee: Bayer Aktiengesellschaft, Leverkusen, Fed. Rep. of Germany

[21] Appl. No.: 558,668

[22] Filed: Dec. 6, 1983

[30] Foreign Application Priority Data

Dec. 28, 1982 [DE] Fed. Rep. of Germany ....... 3248331

[51] Int. Cl.³ ................................................ C08J 9/36
[52] U.S. Cl. ...................................... 521/53; 521/139; 521/146
[58] Field of Search ...................... 521/53, 139, 56, 60

[56] References Cited

U.S. PATENT DOCUMENTS 3,948,821  4/1976  de Benneville ........................ 521/53
4,246,351  1/1981  Miyake et al. ........................ 521/53
4,266,030  5/1981  Tschaug et al. ...................... 521/53

Primary Examiner—Morton Foelak
Attorney, Agent, or Firm—Sprung, Horn, Kramer & Woods

[57] ABSTRACT

The invention relates to SO₃ adducts with imides, which are sparingly soluble or insoluble in water, of the formula

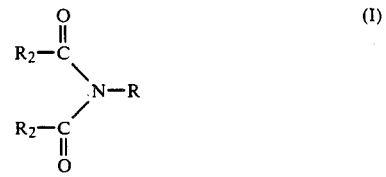

in which $R_1$, $R_2$ and R have the meaning indicated in the description, a process for the preparation of the adducts and their use as sulphonating agents.

2 Claims, No Drawings

SO₃/IMIDE ADDUCTS, PROCESS FOR THEIR PREPARATION AND THEIR USE AS SULPHONATING AGENTS

The invention relates to new SO₃ adducts, their preparation and their use as sulphonating agents.

It is known that SO₃ can form complexes with adduct-formers and that these SO₃ adducts can be used as sulphonating agents (see, for example, the review by E. E. Gilbert in Chemical Reviews, vol. 62, 1962, pages 550 ff.). The adduct-formers which have been used are tertiary amines, tertiary amides, heterocyclic compounds containing nitrogen and/or oxygen and/or sulphur, but also ethers and even benzoic acid.

These known SO₃ adducts have the disadvantage that frequently the SO₃ in them is so strongly deactivated that its reactivity is no longer sufficient for the sulphonation of compounds which are difficult to sulphonate. Moreover, after sulphonation is complete, the adduct-formers can be recovered, if at all, only with considerable losses. As a result of this incomplete recovery, the sulphonations are, on the one hand, costly, and on the other hand, lead to pollution of effluents with adduct-formers.

It has now been found that SO₃ adducts having considerably improved properties and no longer having the disadvantages detailed above are obtained by now employing, instead of the adduct-formers hitherto used, particular imides as the adduct-formers.

The invention relates to SO₃ adducts with imides, which are sparingly soluble or insoluble in water, of the FORMULA

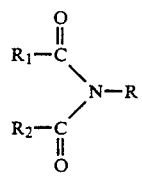 (I)

in which $R_1$ and $R_2$, independently of one another, represent an optionally substituted phenyl radical, or together form an optionally substituted 1,2-phenylene radical, an alkylene radical of the formula $-(CH_2)_m-$, in which m is 2, 3 or 4, or an ethenylene radical of the formula

in which $R_3$ and $R_4$, independently of one another, denote hydrogen, halogen or $C_1-C_4$-alkyl, or together form a 1,4-butylene radical; and R represents an optionally substituted alkyl, cycloalkyl, benzyl or phenyl radical, an acyl radical derived from a monocarboxylic acid, or a radical of the formula

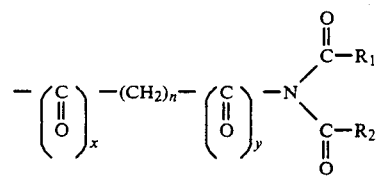

in which $R_1$ and $R_2$ have the meaning indicated above, x and y, independently of one another, represent 0 or 1, and n can assume the values 0, 2, 3, 4, 5 or 6 with the proviso that x, y and n may not all be 0 at the same time, and that x and y must be identical when n is 2, 3, 4, 5 or 6.

The adducts contain 1 to 3 molecules of SO₃ per imide group.

The SO₃/imide adducts according to the invention are distinguished by being able to contain more SO₃ (up to 3 moles of SO₃ per mole of imide group), by the SO₃ in the adducts being so reactive that it is even able to sulphonate compounds which are difficult to sulphonate, such as benzene, biphenyl, naphthalene or polystyrenes, and by the adducts having, in spite of their high reactivity, a considerably improved selectivity compared with the selectivity of SO₃.

Since the adduct-formers according to the invention are sparingly soluble or insoluble in water, it is no problem to recover them without losses. The recovered adduct-formers can then be re-used. Thus, the sulphonations carried out using the SO₃/imide adducts according to the invention are not only more economic than the sulphonations carried out with the known SO₃/imide adducts, they are also more ecologically acceptable, since the adduct-formers according to the invention do not pollute effluents.

Particulary suitable substituents for the phenyl radicals or the 1,2-phenylene radical of $R_1$ and $R_2$ and the benzyl and the phenyl radical of R are those which are inert to SO₃. Moreover, it is advantageous if the substituents decrease the reactivity of the benzene ring. Examples of substituents of this type are lower alkyl groups, such as the methyl group; lower halogenoalkyl groups, such as the trifluoromethyl group; halogen atoms, such as fluorine and chlorine atoms; and the nitro group.

Examples of optionally substituted phenyl radicals which may be mentioned for $R_1$, $R_2$ and R are: the phenyl, tolyl, xylyl, trifluoromethylphenyl, chlorophenyl, dichlorophenyl, fluorophenyl and nitrophenyl radicals.

Examples of optionally substituted 1,2-phenylene radicals which may be determined for $R_1$ and $R_2$ are the monochloro- and dichloro-1,2-phenylene radicals; the monofluoro- and difluoro-1,2-phenylene radicals and the mononitro-and dinitro-1,2-phenylene radicals.

Examples of optionally substituted benzyl radicals which may be mentioned for R are: the benzyl,α-methylbenzyl, the 2-, 3- or 4-methylbenzyl, chlorobenzyl, dichlorobenzyl, trifluoromethylbenzyl and sulphobenzyl radicals. The benzyl radical can also be bonded in the 4 position to a cross-linked polyethylene chain. Imides of the formula (I) in which R represents a benzyl radical of this type bonded to a cross-linked polyethylene chain are insoluble high molecular weight compounds.

Examples of optionally substituted alkyl radicals which may be mentioned for R are: $C_1-C_{12}$-alkyl radicals, such as the methyl, ethyl, propyl, butyl, pentyl, hexyl and 2-ethylhexyl radicals, and halogenated, preferably chlorinated and/or fluorinated, $C_1-C_{12}$-alkyl radicals, such as the chloromethyl, dichloromethyl, trichloromethyl, fluoromethyl, difluoromethyl and trifluoromethyl radicals.

Examples of optionally substituted cycloalkyl radicals which may be mentioned for R are: $C_5-C_{12}$- cycloalkyl radicals, such as the cyclohexyl, methylcyclohexyl, dimethylcyclohexyl and tert.-butylcyclohexyl radicals, and halogenated, preferably chlorinated and/or fluorinated, $C_5-C_{12}$-cycloalkyl radicals, such as the chlorocyclohexyl, dichlorocyclohexyl and trichloromethylcyclohexyl radicals.

Acyl radicals of monocarboxylic acids which may be particularly mentioned for R are acyl radicals of aliphatic $C_1-C_4$-monocarboxylic acids, for example the formyl, acetyl or propionyl radical, and an example of an acyl radical of an aromatic monocarboxylic acid which may be mentioned is the benzoyl radical.

The $SO_3$/imide adducts according to the invention can be either monomolecular compounds or high molecular weight compounds, depending on whether the imide used as the adduct-former is monomolecular or of high molecular weight.

The monomolecular $SO_3$/imide adducts according to the invention (type A of the $SO_3$/imide adducts according to the invention) are soluble in organic solvents as are customarily used for sulphonation with $SO_3$ and thus sulphonation in a homogeneous phase is possible. The monomolecular $SO_3$/imide adducts are derived from imides of the formula (I) indicated above as the adduct-former, in which $R_1$, $R_2$ and R have the meaning indicated under formula (I) with the proviso that R may not represent an optionally substituted benzyl radical which is bonded to a cross-linked polyethylene chain. The monomolecular $SO_3$/imide adducts according to the invention preferably contain 1 to 2 molecules of $SO_3$ per group.

Those $SO_3$/imide adducts of the type A which are derived from imides of the formula (I) as the adduct-former, in which R represents a $C_1-C_4$-alkyl, a cyclohexyl, a

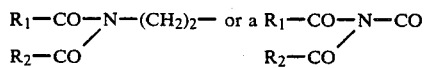

preferred.

The high molecular weight $SO_3$/imide adducts according to the invention (type B of the $SO_3$/imide adducts according to the invention) are insoluble in all solvents. Thus they are used for sulphonations in heterogeneous phases.

The high molecular weight $SO_3$/imide adducts according to the invention are derived from imides of the formula (I) as adduct-formers, in which $R_1$ and $R_2$ have the meaning indicated under formula (I) and R represents an optionally substituted benzyl radical which is bonded to a cross-linked polyethylene chain. The high molecular weight $SO_3$/imide adducts contain 1 to 3, preferably 3, molecules of $SO_3$ per imide group.

Because of their ready accessibility, those $SO_3$/imide adducts of type B which are derived from imides of the formula (I) as the adduct-former, in which $R_1$ and $R_2$ form an optionally substituted 1,2-phenylene radical and R represents an optionally substituted benzyl radical which is bonded to a cross-linked polyethylene chain, area preferred. The preferred imides of type B are produced as intermediates in the preparation of anion exchangers by amidomethylation of cross-linked polystyrenes in the form of beads (see Ullmanns Enzyklopadie der technischen Chemie (Ullmann's Encyclopedia of Industrial Chemistry), 14th edition, vol. 13, page 302). Imidoalkylation products of macroporous polystyrene bead polymers, which have been cross-linked with 3 to 12% by weight of a cross-linking agent, for example divinylbenzene, are used as adduct-formers for the preferred $SO_3$/imide adducts of type B. Imidoalkylation products of those cross-linked macroporous polystyrene bead polymers which have been prepared using about 40 to 100% weight, preferably 50 to 90% by weight, relative to the total mixture of monomers, of a pore-forming component (precipitant or swelling agent for the polymer) are preferably employed.

The invention also relates to a process for the preparation of the $SO_3$/imide adducts according to the invention. The process comprises reacting imides of the formula (I) in the presence of organic solvents, which are inert to $SO_3$, with the amount of $SO_3$ necessary for the desired loading, 1 to 3 moles of $SO_3$, per mole of imide group, at temperatures from 0 to 80° C., preferably 20° to 60° C.

Organic solvents which have proved to be inert to $SO_3$ are halogenated hydrocarbons, especially aliphatic halogenated hydrocarbons, such as methylene chloride, chloroform, carbon tetrachloride, 1,2-dichloroethane, 1,1,2-trichloroethylene and 1,1,2, 2-tetrachloroethane. 1,2-dichloroethane and methylene chloride are preferably used.

The organic solvents are employed in an amount such that the solutions or suspensions of the imides of the formula (I) produced can be easily stirred and easily cooled; in general, 1 to 20, preferably 5 to 10, parts by weight of solvent to 1 part by weight of imide have proved to be suitable.

Addition of $SO_3$ to the imides of the formula (I) takes place very smoothly and rapidly. In general, the adduct formation is complete within 0.5 to 3 hours of mixing the imide and $SO_3$. The adducts according to the invention can either be separated out of the reaction solution mechanically, for example by filtering off or by decanting the reaction solution, or can be isolated by distilling out the organic solvent. After careful washing with fresh organic solvent, the $SO_3$/imide adducts according to the invention are produced in the form of a greyish-white powder (type A) or in the form of a pale grey bead polymer (type B). The $SO_3$/imide adducts according to the invention are generally characterised by elemental analysis, especially by determination of the sulphur value, and by titration of the bound $SO_3$.

The $SO_3$/imide adducts of type A according to the invention are also characterized by their $^1H$ NMR spectrum being shifted in the magnetic field compared with the $^1H$ NMR spectrum of the imide from which they are derived. The imides of the formula (I) which are necessary for the preparation of the $SO_3$/imide adducts according to the invention and the preparation of these imides are known (see Sachs, Chem.Ber. 31, 1228 and Evans, Dehn. J.Amer. Chem.Soc. 51, page 3652 for the preparation of the monomolecular imides, and Ullmanns Enzyklopadie der technischen Chemie, 14th edition, vol. 13, page 302 for the preparation of the high molecular weight imides).

Isolation of the $SO_3$/imide adducts is, in most cases, unnecessary for their use as sulphonating agents; on the contrary, the $SO_3$/imide adducts according to the invention can be used directly for the sulphonation in the form of their solutions in the organic solvents inert to $SO_3$.

The invention also relates to the use of the $SO_3$/imide adducts according to the invention as sulphonating agents. The process according to the invention for sulphonating organic compounds using the $SO_3$/imide adducts according to the invention is particularly suitable for the sulphonation of aromatic hydrocarbons, such as benzene, naphthalene, anthracene, biphenyl, diphenylalkanes and alkylaromatics, such as toluene, xylene, dodecylbenzene or substituted aromatic hydrocarbons, such as halogenated aromatics, phenols, phenol ethers, diphenyl ether, diphenyl thioether, aromatic amines, N-alkylated aromatic amines, and multi-functional substituted aromatic compounds, such as aminophenols and aminophenol ethers.

In the case of the diphenyl derivatives (such as biphenyl, diphenylalkanes and diphenyl ether), the sulphonation with the $SO_3$/imide adducts according to the invention can lead to monosulphonic or disulphonic acids (for example 4,4-disulphonic acids) as selected, and these can be converted into the corresponding amino or hydroxy compounds by known processes.

The sulphonations according to the invention are generally carried out in such a manner that the compound to be sulphonated is added to a solution or suspension of the $SO_3$/imide complex and this mixturej is stirred at 0° to 80° C., preferably at 20° to 30° C., for 30 minutes to 5 hours. The reaction mixture is then worked up.

When using the monomolecular $SO_3$/imide adducts, the following procedure has been found to be particularly useful for working up:

The reaction solutions are extracted with water. In order to isolate the formed sulphonic acids from the aqueous extracts, the aqueous solutions are evaporated to dryness, where appropriate after neutralisation with customary bases, for example alkali metal hydroxides or alkaline earth metal hydroxides.

The organic phases remaining after extraction with water contain the imide used as the adduct-former and, where appropriate, non-sulphonated starting compound.

In order to recover the imide, the organic solvent is distilled off and the mixture of imide and starting compound remaining as a residue is separated into the imide and starting compound by known methods, for example by distillation. The imide can then be used again for renewed preparation of the $SO_3$/imide adduct.

Since the sulphonation using the $SO_3$/imide adducts according to the invention takes place virtually completely, and thus the amounts of unsulphonated compound are negligibly small, it is possible in most cases to dispense with working up the organic phase and, after removal of the residual water in it, to use the organic phase directly for renewed preparation of the $SO_3$/imide adduct and, following the formation of the $SO_3$/imide adduct, to use it in turn for sulphonation. This means that the organic phase, and the imide contained therein, is recycled. In phase 1 of the cycle (preparation of the $SO_3$/imide adduct), the imide is loaded with $SO_3$, and in phase 2 of the cycle (sulphonation), the imide passes the $SO_3$ which it has taken up on to the compound to be sulphonated. When recycling in this manner, possible accumulation of impurities in the organic phase can be prevented by removing and purifying a part stream and returning to the organic phase amounts of pure solvent and imide corresponding to the amounts of organic solvent and imide removed.

When using the high molecular weight $SO_3$/imide adducts, the following procedure has been found to be particularly useful for working up:

After sulphonation is complete, the high molecular weight imide is mechanically separated out of the reaction solution, rinsed with solvent if appropriate, and then used again for renewed adduct formation.

The reaction solution remaining after removal of the imide is extracted with water to remove the sulphonic acids. The sulphonic acids are isolated as such or in the form of their salts from the aqueous extracts as described above.

The organic solvent remaining after extraction of the sulphonic acids from the reaction solutions is, after removal of the water, distilled out and employed again or merely dried and used again directly.

When there is more than 1 molecule of $SO_3$ per imide group in the $SO_3$/imide adducts according to the invention, then the individual $SO_3$ molecules are bound to the imide group with varying strengths. The first $SO_3$ molecule is bound most strongly to the imide group while the third $SO_3$ molecule is bound least strongly. Thus, it is preferable to use for particularly selective sulphonations those $SO_3$/imide adducts which only contain 1 molecule of $SO_3$ per imide group.

EXAMPLE 1

16.1 g (0.1 mol) of N-methylphthalimide and 4.2 ml (0.1 mol) of sulphur trioxide are mixed in 50 ml of dichloromethane, with stirring and cooling at 0° to +20° C. A white flocculent precipitate forms. The dichloromethane is then distilled off in vacuo at 20° C.

23.5 g (98% of theory) of the $SO_3$/N-methylphthalimide 1:1 adduct are obtained in the form of a solid white residue. The adduct is hygroscopic and slowly becomes liquid on standing in the air.

In the same manner as the $SO_3$/N-methylphthalimide 1:1 adduct described above, the 1:1 adducts of $SO_3$ to N-ethylphthalimide, N-n-propylphthalimide and N-sec.-butylphthalimide were prepared.

The yields of these 1:1 adducts were likewise about 98% of theory. All three products were likewise produced in the form of white hygroscopic solids.

EXAMPLE 2

25.1 g (0.1 mol) of N-benzoylphthalimide and 4.2 ml (0.1 mol) of sulphur trioxide are reacted together as described in Example 1. A yellow flocculent precipitate is produced. After distilling off the dichloromethane, 31.4 g (96% of theory) of the $SO_3$/N-benzoylphthalimide 1:1 adduct are obtained in the form of a yellow solid. The adduct is hygroscopic and becomes liquid on standing in the air.

EXAMPLE 3

14.1 g (0.1 mol) of N-n-propylsuccinimide and 4.2 ml (0.1 mol) of sulphur trioxide are reacted together as described in Example 1. A pink coloured precipitate is formed. After distilling off the dichloromethane, 21 g (97% of theory) of the $SO_3$/N-n-propylsuccinimide 1:1 adduct are obtained in the form of a pale pink coloured solid.

EXAMPLE 4

16 g (0.1 mol) of N-methylphthalimide are mixed with a solution of 13.3 ml (0.3 mol) of sulphur trioxide in 200 ml of dichloromethane, with stirring and cooling at 0° to 20° C. The dichloromethane is then distilled off and the residue is heated at 80° C. in order to remove unbound sulphur trioxide.

After cooling down to room temperature, 32 g (97% of theory) of $SO_3$/N-methylphthalimide 2:1 adduct are obtained in the form of a yellow crystalline solid. The 2:1 adduct is very hygroscopic and becomes liquid on standing in the air.

The sulphur content of the product is 19.9% (theoretical figure: 20.0%).

EXAMPLE 5

60 g (0.21 mol) of a phthalimidomethylated polystyrene bead polymer which is cross-linked with 8% by weight of divinylbenzene and which has been made macroporous with 80% by weight of isododecane (number of phthalimidomethyl groups per aromatic nucleus in the polystyrene: 0.9) are mixed with a solution of 37 ml (0.88 mol) of sulphur trioxide in 200 ml of dichloromethane, with stirring and cooling. The mixture is stirred at 15° to 30° C. for 2 hours. The bead polymer loaded with $SO_3$ is then filtered off, rinsed with a little dichloromethane and dried in vacuo at room temperature.

130 g of $SO_3$/imide resin 3:1 adduct are obtained.

Analysis of this $SO_3$/imide resin 3:1 adduct shows that, due to the treatment with sulphur trioxide, the phthalimidomethylated polystyrene was, on the one hand, sulphonated (number of sulphonic acid groups per aromatic nucleus in the polystyrene: 0.9) and, on the other hand, contains 3 bound molecules of $SO_3$ per imide group.

When, instead of the phthalimidomethylated polystyrene bead polymer used, the same amount of a phthalimidomethylated polystyrene bead polymer, which had been cross-linked with 5% by weight of divinylbenzene and made macroporous with 60% by weight of isododecane, or a phthalimidomethylated polystyrene bead polymer, which had been cross-linked with 6% by weight of divinylbenzene and made macroporous with 70% by weight of isododecane, (the number of phthalimido groups per aromatic nucleus was about 0.9 in both resins) was employed, then $SO_3$/imide resin 3:1 adducts having virtually identical properties were obtained.

EXAMPLE 6

32 g (0.2 mol) of N-methylphthalimide are mixed with solution of 8.3 ml (0.2 mol) of sulphur trioxide in 200 ml of 1,2-dichloroethane, with stirring and cooling at 0° to 20° C. A solution of 25 g (0.2 mol) of naphthalene in 50 ml of 1,2-dichloroethane is added dropwise, with stirring and cooling at 0° to 20° C., to the solution produced. The clear solution is stirred at 80° C. (reflux temperatures) for 1 hour.

The reaction solution is then extracted 3 times with 100 ml of water each time. The combined aqueous extracts are neutralised with 32 g of 25% strength aqueous sodium hydroxide solution and then evaporated to dryness on a rotary evaporator. 45.5 g (99% of theory) of naphthalene-1-sulphonic acid (sodium salt) are obtained in the form of a white powder.

The dichloroethane solution remaining after the extraction with water is evaporated to dryness in a rotary evaporator. 31.5 g (98% of the amount employed) of N-methylphthalimide are recovered.

On sulphonation of 0.2 mol of naphthalene with 0.2 mol of free sulphur trioxide, only 55% of theory of naphthalene-1-sulphonic acid (sodium salt) were obtained, with, on the other hand, as by-products, 21% of theory of naphthalene disulphonic acid (sodium salt) and 12% of theory of dinaphthyl sulphone.

The followinhg were sulphonated in the manner described for the sulphonation of naphthalene with the $SO_3$/N-methylphthalimide adduct:

(a) naphthalene with the 1:1 adduct of $SO_3$ to N-butylphthalimide,
(b) biphenyl with the 1:1 adduct of $SO_3$ to N-methylphthalimide and
(c) n-decanol with the 1:1 adduct of $SO_3$ to N-methylphthalimide.

In case (a) 89 g (97% of theory) of naphthalene-1-sulphonic acid (sodium salt) were obtained and 56 g (98.9%) of the N-methylphthalimide used were recovered.

In case (b) 40 g (78% of theory) of biphenyl-4-sulphonic acid (sodium salt) were obtained and 32 g (100%) of the adduct-former N-methylphthalimide were recovered.

In case (c) 52 g (100% of theory) of the sulphate of dodecanol (sodium salt) were obtained and 31 g (97%) of the N-methylphthalimide were recovered.

EXAMPLE 7

25.1 g (0.1 mol) of N-benzoylphthalimide are mixed with a solution of 4.2 ml (0.1 mol) of sulphur trioxide in 100 ml of 1,2-dichloroethane, with stirring and cooling at 0° to +20° C. 7.8 g (0.1 mol) of benzene are added dropwise to the solution with stirring and cooling at 0 to 20° C.

The reaction solution is then worked up as described in Example 6.

17.1 g (95% of theory) of benzenesulphonic acid (sodium salt) are obtained in the form of a white powder.

24 g (96% of N-benzoylphthalimide are recovered.

EXAMPLE 8

14 g (0.1 mol) of N-propylsuccinimide are mixed with a solution of 4.2 ml (0.1 mol) of sulphur trioxide in 100 ml of 1,2-dichloroethane, with stirring and cooling at 0° to 20° C. 15 g (0.1 mol) of biphenyl are introduced into the solution with stirring and cooling at 0° 20° C.

The reaction solution is worked up as described in Example 1. 23.1 g (90% of theory) of biphenyl-4-sulphonic acid (sodium salt) are obtained in the form of a white powder, and 13.5 g (96.5%) of N-propylsuccinimide are recovered.

EXAMPLE 9

60 g (0.21 mol) of the phthalimidomethylated polystyrene bead polymer used for adduct-formation in Example 5 are mixed with a solution of 37 ml (0.88 mol) of sulphur trioxide in 200 ml of dichloromethane, with stirring and cooling at 0° to 20° C. 58 g (0.63 mol) of toluene are added to the mixture with stirring and the mixture is stirred at 0° to 20° C. for 1 hour. The bead polymer is then filtered off from the reaction solution. The filtrate is extracted with 300 ml of water and the is neutralised with 0.53 mol of NaOH. The aqueous extract solution is evaporated to dryness.

93.1 g (89% of theory) of toluene sulphonic acid (sodium salt) are obtained.

Working up the organic phase provides 5.7 g of di-tolyl sulphone.

The imide resin is used again for the preparation of the SO$_3$/imide resin 3:1 adduct. Since SO$_3$ is no longer consumed to sulphonate the imide resin, only that amount of SO$_3$ calculated for formation of the 3:1 adduct is necessary for adduct formation.

EXAMPLE 10

The procedure is as described in Example 9 but, instead of 58 g of toluene, 29 g (0.63 mol) of ethanol are added.

75 g (80% of theory) of ethanol sulphate (sodium salt) are obtained in the form of a white powder.

EXAMPLE 11

The procdure is as described in Example 9 but, instead of 58 g of toluene, 67 g of xylene are used.

116 g (89% of theory) of xylene sulphonic acid (sodium salt) are obtained in the form of a white powder.

Working up the organic phase provides 5 g of dixylyl sulphone.

EXAMPLE 12

32 g (0.2 mol) of N-methylphthalimide are mixed with a solution of 8.3 ml (0.2 mol) of sulphur trioxide in 200 ml of dichloromethane, with stirring and cooling at 0° to 20° C. A solution of 17 g (0.1 mol) of diphenyl ether in 50 ml of dichloromethane is added dropwise, with stirring and cooling at 0° to 20° C., to the solution produced. The clear solution is stirred at 40° C. (reflux temperature) for 1 hour.

The reaction solution is then worked up as described in Example 6.

32 g (97% of theory) of diphenyl ether 4,4-disulphonic acid (disodium salt) are obtained in the form of a white powder.

31 g (97%) of N-methylphthalimide are recovered.

What is claimed is:

1. A SO$_3$ adduct with an imide, which is sparingly soluble or insoluble in water, of the formula

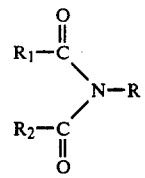

in which R$_1$ and R$_2$, independently of one another, are an optionally substituted phenyl radical, or together form an optionally substituted 1,2-phenylene radical, an alkylene radical of the formula —(CH$_2$)$_m$—, in which m is 2,3 or 4, or an ethenylene radical of the formula

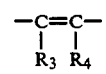

in which
R$_3$ and R$_4$, independently of one another, are hydrogen, halogen or C$_1$–C$_4$-alkyl, or together form a 1,4-butylene radical; and
R is an optionally substituted benzyl radical, which is bonded to a cross-linked polyethylene chain,
the imide being an imidoalkylation product of a macroporous polystyrene bead polymer cross-linked with 3 to 12% by weight of cross-linking agent.

2. An adduct according to claim 1, in which R$_1$ and R$_2$ together form an optionally substituted 1,2-phenylene radical.

* * * * *